(12) United States Patent
Guo et al.

(10) Patent No.: US 12,214,021 B2
(45) Date of Patent: Feb. 4, 2025

(54) STUDY ON LACTOFERRIN REGULATION OF BONE FORMATION BY MEANS OF VITAMIN D RECEPTOR

(71) Applicant: CHINA AGRICULTURAL UNIVERSITY, Beijing (CN)

(72) Inventors: Huiyuan Guo, Beijing (CN); Yixuan Li, Beijing (CN); Hao Zhang, Beijing (CN); Liang Zhao, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 1028 days.

(21) Appl. No.: 17/059,565

(22) PCT Filed: May 31, 2018

(86) PCT No.: PCT/CN2018/089332
§ 371 (c)(1),
(2) Date: Nov. 30, 2020

(87) PCT Pub. No.: WO2019/227421
PCT Pub. Date: Dec. 5, 2019

(65) Prior Publication Data
US 2021/0228689 A1    Jul. 29, 2021

(51) Int. Cl.
| | | |
|---|---|---|
| *A61K 38/40* | (2006.01) | |
| *A23L 33/155* | (2016.01) | |
| *A23L 33/17* | (2016.01) | |
| *A61K 31/59* | (2006.01) | |
| *A61K 31/593* | (2006.01) | |
| *A61P 19/08* | (2006.01) | |
| *A61P 19/10* | (2006.01) | |

(52) U.S. Cl.
CPC ............ *A61K 38/40* (2013.01); *A61K 31/593* (2013.01); *A61P 19/08* (2018.01)

(58) Field of Classification Search
CPC ........ A61K 38/40; A61K 31/593; A61P 19/08
See application file for complete search history.

(56) References Cited

FOREIGN PATENT DOCUMENTS

| CN | 105399816 | 3/2016 |
|---|---|---|
| CN | 108671225 | 10/2018 |

OTHER PUBLICATIONS

Naot et al., "Lactoferrin—A Novel Bone Growth Factor," Clinical Medicine & Research 3:93-101 (2005) (Year: 2005).*
Gou et al., "Orally Administered Lactoferrin Preserves Bone Mass and Microarchitecture in Ovariectomized Rats," J. Nutr. 139: 958-964 (2009) (Year: 2009).*
Nordin et al., "Osteoporosis and Vitamin D," J. Cellular Biochem. 49:19-25 (1992) (Year: 1992).*
PubChem CID 5371933, 1,25 Dihydroxyvitamin D3, accessed Apr. 4, 2024 at URL pubchem.ncbi.nlm.nih.gov/compound/1_25-Dihydroxyvitamin-D3, 41 pages (Year: 2024).*
WIPO, ISR for PCT/CN2018/089332, Mar. 11, 2019.
Chen et al., "The present condition of drug therapy on osteoporosis," Chinese Journal of Modern Applied Pharmacy, 2001, vol. 18, No. 2, 4 pages.
Chen et al., "The best concentration and the best time of lactoferrin for the stimulation of osteoblast proliferation and differentiation," Chinese Journal of Osteoporosis, 2015, vol. 21, No. 2, pp. 142-146.
Du et al., "Effect of bovine lactoferrin on the bone metabolism in ovariectomized rats," Fujian Medical Journal, 2011, vol. 33, No. 2, pp. 5-8.
Hou et al., "Bovine lactoferrin improves bone mass and microstructure in ovariectomized rats via OPG/RANKL/RANK pathway," Acta Pharmacologica Sinica, 2012, vol. 33, pp. 1277-1284.
WIPO, International Search Report for PCT/CN2018/089332, Mar. 11, 2019.

\* cited by examiner

*Primary Examiner* — Julie Ha
*Assistant Examiner* — Kristina M Hellman
(74) *Attorney, Agent, or Firm* — Hodgson Russ LLP

(57) ABSTRACT

A use of lactoferrin in the preparation of a food or drug, the food or drug being used for activating a VDR signaling pathway, which is used for the treatment of bone disease, bone disease comprising: osteoporosis, bone damage, loss of bone calcium, incomplete bone development and bone abnormalities. The present invention further comprises screening for drugs that are used to promote osteoblast proliferation and differentiation by using an active state of the VDR signaling pathway.

12 Claims, 9 Drawing Sheets

STUDY ON LACTOFERRIN REGULATION OF BONE FORMATION BY MEANS OF VITAMIN D RECEPTOR

CROSS-REFERENCE TO RELATED APPLICATIONS

The present application is a national phase entry under 35 USC § 371 of International Application PCT/CN2018/089332, filed on May 31, 2018, the entire disclosure of which is incorporated by reference herein.

FIELD

The present disclosure relates to the field of biology. Specifically, the present disclosure relates to the study on lactoferrin regulating bone formation through vitamin D receptors. More specifically, the present disclosure relates to the use of lactoferrin in preparing a food or medicament, a method for promoting osteoblast proliferation and differentiation, a medicament, a pharmaceutical combination, a method for screening a drug, and a method of treating a bone disease.

BACKGROUND

Lactoferrin (LF) is a natural glycoprotein with a molecular weight of 78 KDa in milk. As a transferrin, it has homology in the amino acid sequence with transferrin in blood. LF is a new functional protein in milk, and can exert different biological functions in different physiological environments, such as antibacterial, antiviral, regulating iron metabolism, promoting angiogenesis, promoting bone growth, regulating intestinal flora, and participating in immune regulation, etc. In addition, LF can also regulate the proliferation and differentiation of a variety of cells. In recent years, LF has been widely used as a natural bone-promoting protein in a variety of foods, especially as strengthening additives in infant formula.

VDR, a member of the nuclear receptor family, is a ligand-dependent nuclear transcription factor in a variety of human cells. It is currently believed that VDR can be expressed in all nucleated cells. The active forms of vitamin D are $25OHD_3$ and $1.25(OH)_2D_3$. $1.25(OH)_2D_3$ is the most active metabolite and can not only regulate bone metabolism by regulating calcium and phosphorus balance, but also has the function of promoting growth, anti-inflammatory and regulating the body's immune function. VDR is a hot topic in the field of bone health research in recent years. It can regulate bone metabolism by acting on both bone synthesis and breakdown, and it is present in both osteoblasts and osteoclasts and participates in both osteoblast differentiation and osteoclastic bone resorption. It follows that, VDR plays an important role in calcium and phosphorus balance and bone metabolism in the body. In addition, VDR can also regulate the proliferation and differentiation of tissue cells and the process of immune regulation.

VDR is an important target for mediating the physiological function of $1.25(OH)_2D_3$. At present, it has been found that $1.25(OH)_2D_3$ is a classic ligand of VDR and can only exert its physiological functions under the regulation of VDR. However, the ligands of VDR are not merely $1.25(OH)_2D_3$, and many $1.25(OH)_2D_3$ analogs can also be used as ligands of VDR. After the ligand enters the cell to activate the VDR, the VDR enters the nucleus with the vitamin D binding protein and binds to the retinoic acid X receptor (RXR) to form a dimeric complex. The complex binds with specific vitamin D response elements (VDREs) to regulate the process of cell proliferation and differentiation, bone metabolism balance, and immune regulation.

However, the bone-promoting mechanism of lactoferrin and VDR signaling pathways is not fully understood, and remains to be studied.

SUMMARY

The present disclosure aims to solve at least one of the technical problems in the prior art to at least some extent.

It should be noted that the present disclosure was completed based on the following findings of the inventors:

The intake of vitamin D by the body will increase the absorption of calcium and phosphorus in the small intestine, resulting in increased blood calcium and phosphorus levels. High blood phosphorus easily destroys the homeostasis of calcium, and high blood calcium can easily cause hyperparathyroidism, reduced nerve and muscle excitability, enhanced myocardial membrane barrier effect, decreased myocardial excitability and conductivity, renal dysfunction, etc., causing serious damage to the body. In addition, the elevated parathyroid hormone will increase bone resorption, promote the release of bone calcium, and cause loss of bone calcium.

In view of this, the inventors tried to take lactoferrin instead of vitamin D into the body, and found that there is no increase in blood calcium and phosphorus levels. At the same time, lactoferrin can significantly reduce the contents of calcium and phosphorus in urine, reduce the excretion of calcium and phosphorus, and promote the reabsorption of calcium and phosphorus by the kidney, thereby maintaining blood calcium balance. In addition, lactoferrin can increase the calcium and phosphorus content in the bone by inhibiting the release of bone calcium and promoting the deposition of bone calcium. Further, the inventors have found that lactoferrin can act as a VDR agonist to promote the high expression of VDR genes to activate the VDR signaling pathway, and can regulate the proliferation and differentiation of osteoblasts to promote bone formation. Therefore, lactoferrin can be used instead of vitamin D as a component of food or medicament to effectively promote the proliferation and differentiation of osteoblasts. Lactoferrin has small side effects and is suitable for large-scale applications.

For this reason, in one aspect of the present disclosure, the present disclosure provides the use of lactoferrin in the preparation of a food or medicament. According to an embodiment of the present disclosure, the medicament is used to activate a VDR signaling pathway. The inventors found that lactoferrin can be used as a VDR agonist to promote the high expression of VDR genes to activate the VDR signaling pathway, and can promote the proliferation and differentiation of osteoblasts, inhibit the bone resorption of osteoclasts, or inhibit the release of bone calcium. Therefore, lactoferrin instead of vitamin D as a component of food or medicament has the effects of promoting the deposition of bone calcium, bone formation, and maintaining the balance of blood calcium. Lactoferrin has small side effects and is suitable for large-scale applications.

According to an embodiment of the present disclosure, the above-mentioned use of lactoferrin in the preparation of a food or medicament may have the following additional technical features:

According to an embodiment of the present disclosure, the food or medicament is used to promote the proliferation and differentiation of osteoblasts, inhibit the bone resorption of osteoclasts, or inhibit the release of bone calcium.

According to an embodiment of the present disclosure, the lactoferrin promotes the expression of VDR gene to activate the VDR signaling pathway.

According to an embodiment of the present disclosure, the lactoferrin increases the expression of VDR gene by 25 to 35 times. Therefore, lactoferrin can promote the expression of VDR gene to achieve the purpose of activating the VDR signaling pathway.

According to an embodiment of the present disclosure, the lactoferrin promotes the reabsorption of calcium and phosphorus by the kidney to maintain the calcium balance in the blood. Lactoferrin can significantly reduce the contents of calcium and phosphorus in urine, reduce the excretion of calcium and phosphorus, and promote the reabsorption of calcium and phosphorus by the kidney, thereby maintaining blood calcium balance. In addition, lactoferrin can increase the calcium and phosphorus content in the bone by inhibiting the release of bone calcium and promoting the deposition of bone calcium.

According to an embodiment of the present disclosure, the lactoferrin promotes the expression of VDR gene in the kidney.

According to an embodiment of the present disclosure, the lactoferrin promotes the expression of VDR gene in bone tissue.

According to an embodiment of the present disclosure, the lactoferrin promotes the expression of VDR gene in the colon.

According to an embodiment of the present disclosure, the lactoferrin increase bone mineral density.

According to an embodiment of the present disclosure, the lactoferrin improve the microstructure of trabecular bone. The inventors found that lactoferrin can significantly improve the damaged three-dimensional structure of trabecular bone in mice caused by VD-deficient, and has the effect of activating bone rebuilding and promoting bone formation, and thus can effectively replace the effect of VD on bone health and compensate for bone damage caused by VD-deficient.

According to an embodiment of the present disclosure, the activation of the VDR signaling pathway by the lactoferrin is not regulated by the p38 pathway and the TGF-β/Smads pathway.

The inventors found in previous studies that LF can activate the nuclear transcription factor Runx2 through the PKA-p38 pathway, thereby regulating the differentiation process of osteoblasts. Transforming growth factor β (TGF-β) is a multifunctional cell growth factor, which can mediate the regulation of cell proliferation, differentiation and apoptosis through cell membrane receptors. In addition, TGF-β factor plays an important role in the synthesis of extracellular matrix, immune regulation, and wound healing. The effect of TGF-β on osteogenesis is mainly through the classical Smads pathway. Each subtype of TGF-β family and the receptors thereof play an important role in osteogenesis. The receptors are mainly TGF-β type I receptors and type II receptors. TGF-β I can promote the formation of new bone by promoting the expression of type II collagen in chondrocyte precursor cells, and it can also promote the formation of bone matrix. In addition, TGF-β I can also inhibit osteoclast differentiation by reducing RANKL secreted by osteoblasts, which indicates that TGF-βI can indirectly inhibit bone resorption to increase bone mineral density.

The inventors found in previous studies that activation of the p38 pathway can regulate VDR expression, and that lactoferrin can activate the p38 pathway. However, the inventors found that the p38 pathway is not involved in the promotion of VDR by lactoferrin. Studies have shown that in caco-2 cells, the expression of VDR is co-regulated by the p38 pathway and the TGF/Smads pathway. Furthermore, the inventors found that the promotion effect of lactoferrin on the expression of VDR is not related to the extracellular p38 pathway and the TGF-β/Smads pathway, and may be through other pathways or mainly through intracellular mechanisms.

According to an embodiment of the present disclosure, the activation of the VDR signaling pathway by the lactoferrin is in a cell.

According to an embodiment of the present disclosure, the food or medicament is used to treat a bone disease. The inventors found that lactoferrin can be used as a VDR agonist to promote the high expression of VDR genes to activate the VDR signaling pathway, and can promote the proliferation and differentiation of osteoblasts, inhibit the bone resorption of osteoclasts and inhibit the release of bone calcium.

It should be noted that the term "bone disease" used herein should be understood in a broad sense, and all diseases related to bones belong to bone diseases. In some embodiments, the bone disease includes: osteoporosis, bone damage, loss of bone calcium, incomplete bone development, and skeletal abnormalities.

According to an embodiment of the present disclosure, the dosage of the medicament is 100-1000 mg/kg BW for treating a bone disease.

In another aspect of the present disclosure, the present disclosure provides a method for promoting osteoblast proliferation and differentiation. According to an embodiment of the present disclosure, the method comprises: treating osteoblasts with lactoferrin under suitable conditions. The inventors discovered that by treating osteoblasts with lactoferrin, the lactoferrin activates the VDR signaling pathway, thereby promoting the proliferation and differentiation of osteoblasts, inhibiting bone resorption by osteoclasts, or inhibiting the release of bone calcium.

According to an embodiment of the present disclosure, the method further comprises: providing vitamin D for treating osteoblasts with both vitamin D and lactoferrin. The inventors have found that vitamin D can play a synergistic effect with lactoferrin, thereby promoting the proliferation and differentiation of osteoblasts, inhibiting the bone resorption of osteoclasts, or inhibiting the release of bone calcium.

According to an embodiment of the present disclosure, the vitamin D is provided in the form of 25-OH $D_3$ and/or 1.25$(OH)_2D_3$, and the concentration of the 1.25$(OH)_2D_3$ added is 0.1 to 10 nM. The inventors found that under these conditions, osteoblasts can achieve better proliferation and differentiation.

According to an embodiment of the present disclosure, the treatment lasts 2 to 6 hours. The inventors found that under these conditions, osteoblasts can achieve better proliferation and differentiation.

In yet another aspect of the present disclosure, the present disclosure proposes a medicament. According to an embodiment of the present disclosure, the medicament contains lactoferrin, and the medicament is used to activate a VDR signaling pathway. The inventors found that lactoferrin can be used as a VDR agonist to promote the high expression of VDR genes in order to activate the VDR signaling pathway, promote the proliferation and differentiation of osteoblasts, inhibit the bone resorption of osteoclasts, or inhibit the release of bone calcium effect.

In yet another aspect of the present disclosure, the present disclosure provides a pharmaceutical combination. According to an embodiment of the present disclosure, the pharmaceutical combination comprises the aforementioned medicament and vitamin D. The inventors discovered that lactoferrin activates the VDR signaling pathway, thereby promoting the proliferation and differentiation of osteoblasts. Further, the inventors discovered that vitamin D can play a synergistic effect with lactoferrin to further promote the proliferation and differentiation of osteoblasts and improve the osteogenic effect.

It should be noted that, in the present disclosure, the administration of aforementioned medicament and vitamin D are not strictly limited, and the two can be administered independently or in combination.

In yet another aspect of the present disclosure, the present disclosure provides a method for screening a drug. According to an embodiment of the present disclosure, the drug is used to promote osteoblast proliferation and differentiation, and the method comprises: (1) contacting a candidate drug with osteoblasts; and (2) determining the activation state of the VDR signaling pathway in the osteoblasts before and after the contact to determine whether the candidate drug is a target drug promoting osteoblast proliferation and differentiation; wherein activated VDR signal pathway in the osteoblasts after the contact is the indicator of the candidate drug being the target drug.

The inventors discovered that lactoferrin can activate the VDR signaling pathway to promote the proliferation and differentiation of osteoblasts. Furthermore, by determining whether the VDR signaling pathway is activated in osteoblasts before and after the contact, it is possible to screen for drugs containing lactoferrin. Specifically, if the VDR signaling pathway is activated, it indicates that the target drug is a lactoferrin-containing drug.

According to an embodiment of the present disclosure, the method further comprises in step (2): comparing the expression of VDR gene before and after the contact, wherein increased expression of VDR gene after the contact as compared with that before the contact is the indicator of the candidate drug being the target drug. The inventors found that lactoferrin can promote VDR gene expression and activate VDR signaling pathways to promote the proliferation and differentiation of osteoblasts. Furthermore, by comparing the expression of VDR in osteoblasts before and after the contact, it is possible to screen for drugs containing lactoferrin. Specifically, if the expression level is increased, it indicates that the target drug is a lactoferrin-containing drug.

In yet another aspect of the present disclosure, the present disclosure provides a method of treating a bone disease. According to an embodiment of the present disclosure, the method comprises administering to a patient in need thereof the aforementioned medicament or pharmaceutical combination. The inventors found that lactoferrin activates the VDR signaling pathway, thereby promoting the proliferation and differentiation of osteoblasts, inhibiting bone resorption by osteoclasts, or inhibiting the release of bone calcium. In addition, the inventors discovered that vitamin D can play a synergistic effect with lactoferrin to further promote the proliferation and differentiation of osteoblasts and improve the osteogenic effect. Therefore, by administering a medicament containing lactoferrin or a pharmaceutical combination containing lactoferrin and vitamin D to a patient in need thereof, it is possible to activate the proliferation and differentiation of osteoblasts in the patient, inhibit the bone resorption of osteoclasts, or inhibit the release of bone calcium, so as to achieve the treatment purpose.

It should be noted that the term "patient" used herein should be understood in a broad sense and refers to diseased animals, including humans and livestock.

According to an embodiment of the present disclosure, the dosage of the medicament is 100-1000 mg/kg BW. The inventors have found that a good therapeutic purpose can be achieved under these conditions.

According to an embodiment of the present disclosure, the bone disease comprises osteoporosis, bone damage, loss of bone calcium, incomplete bone development, and bone abnormalities.

The term "treat" or "treatment" or "treating" as used herein refer to a process for obtaining the desired pharmacological and/or physiological effect. The effect may be prophylactic in terms of completely or partially preventing the disease or its symptoms, and/or may be therapeutic in terms of partially or completely curing the disease and/or adverse effects caused by the disease. "Treatment" as used herein is direct to diseases in mammals, particularly humans, including: (a) preventing a disease (e.g., preventing a bone disease) or condition from occurring in individuals who are susceptible to the disease but have not yet been diagnosed with the disease; (b) inhibiting a disease, such as retarding the development of the disease; or (c) alleviating a disease, such as reducing symptoms associated with the disease. "Treatment" as used herein encompasses the administration of drugs or compounds to an individual to treat, cure, alleviate, ameliorate, reduce or inhibit the disease of the individual, including, but not limited to, administering a medicament containing lactoferrin as described herein to an individual in need thereof.

The medicament or the pharmaceutical combination of the present disclosure may further include a pharmaceutically acceptable excipient, carrier, excipient, vehicle, or a combination thereof.

The term "administration" as used herein refers to introduction of a predetermined amount of a substance into a patient by some suitable means. The medicament or the pharmaceutical combination of the present disclosure can be administered by any common route, as long as it can reach the intended tissue. Various modes of administration are contemplated, including peritoneal, intravenous, intramuscular, subcutaneous, cortical, oral, topical, nasal, lung and rectal administration, but the present disclosure is not limited to these exemplary modes of administration.

The administration frequency and dosage of the medicament or the pharmaceutical combination of the present disclosure can be determined by a number of related factors, including the type of disease to be treated, the route of administration, the age, sex and weight of the patient, the severity of the disease, and the type of drug used as the active ingredient. According to some embodiments of the present disclosure, the daily dose can be divided into 1 dose, 2 doses or multiple doses in a suitable form, so as to be administered once, twice or multiple times over the entire time period, as long as a therapeutically effective amount is reached.

Additional aspects and advantages of the present disclosure will be given in part in the following description, and in part become apparent from the following description or be learned through the practice of the present disclosure.

BRIEF DESCRIPTION OF THE DRAWINGS

The above and/or additional aspects and advantages of the present disclosure will become apparent and easily understood from the description of the embodiments in conjunction with the following drawings, in which.

DETAILED DESCRIPTION

The solution of the present disclosure will be explained below with reference to the examples. Those skilled in the art will understand that the following examples are only used to illustrate the present disclosure and should not be considered as limiting the scope of the present disclosure. If specific technology or conditions are not indicated in the examples, the technology or conditions described in the literature in the art or the product descriptions will be used. All reagents or instruments for which the manufacturers are not indicated are conventional commercially available products.

Example 1

1. The Regulatory Effect of Lactoferrin on the VDR Pathway in Osteoblasts.

Figure 1:
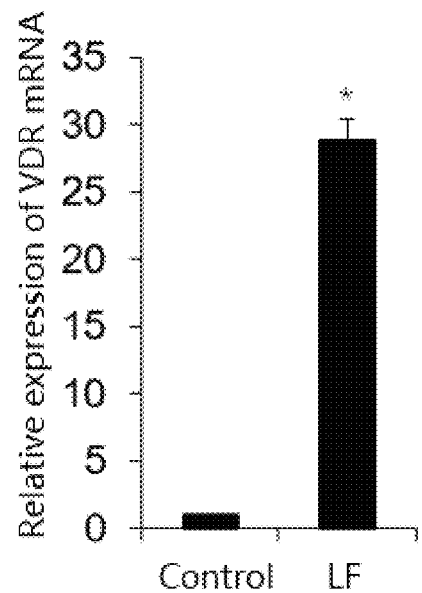
FIG. 1 shows the effect of lactoferrin on the expression of VDR mRNA in osteoblasts according to an embodiment of the present disclosure.

In order to study the regulatory effect of lactoferrin on VDR, the inventors first analyzed the expression of VDR gene in MC3T3-E1 cells under LF stimulation. As shown in FIG. 1, LF can promote VDR expression up to 30-fold at mRNA levels.

Figure 2:
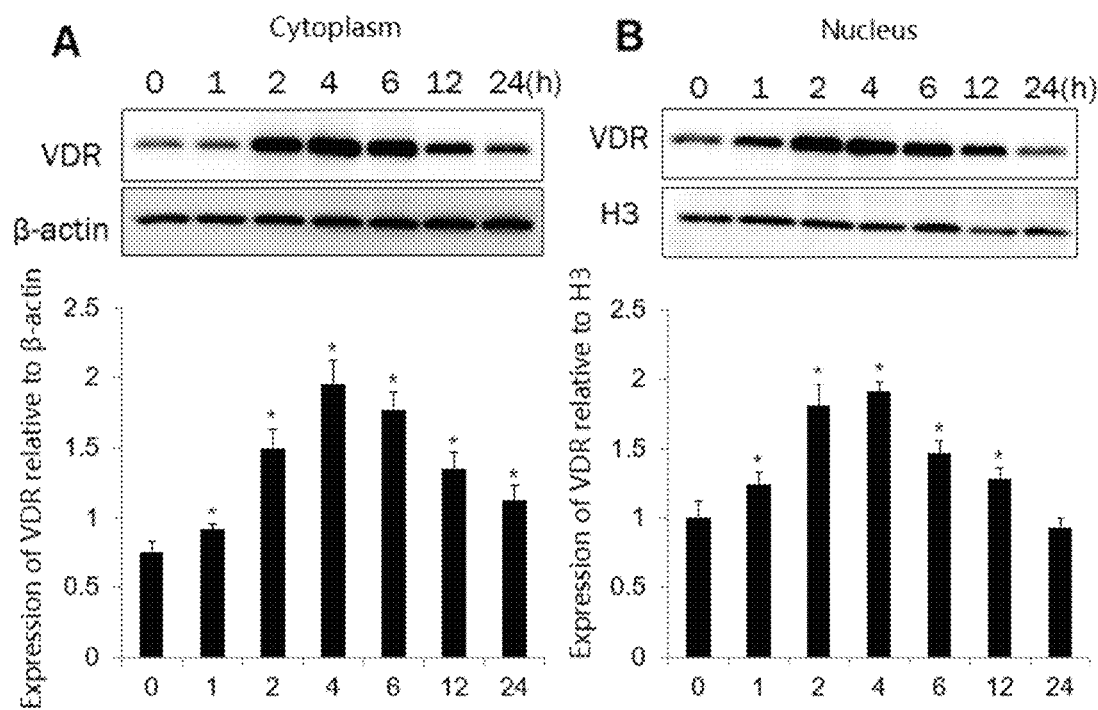
FIGS. 2A and 2B show the effect of lactoferrin for different treating duration on the expression of VDR in osteoblasts according to an embodiment of the present disclosure.

After verifying that LF promotes high expression of VDR at the transcription level, it is further verified at the protein level. VDR exists in the cytoplasm and nucleus, but plays a major role in the nucleus. The inventors stimulated osteoblasts for different times using LF to measure the expression of VDR in the cytoplasm and nucleus. As shown in FIG. 2, VDR expression in the cytoplasm is significantly increased after treating osteoblasts with LF for two hours, and reaches the maximum after 4 hours, and began to normalize after 12 hours. In the nucleus, VDR expression began to increase at 1 hour after LF treatment, and reaches the maximum at 2-6 h.

Figure 3:
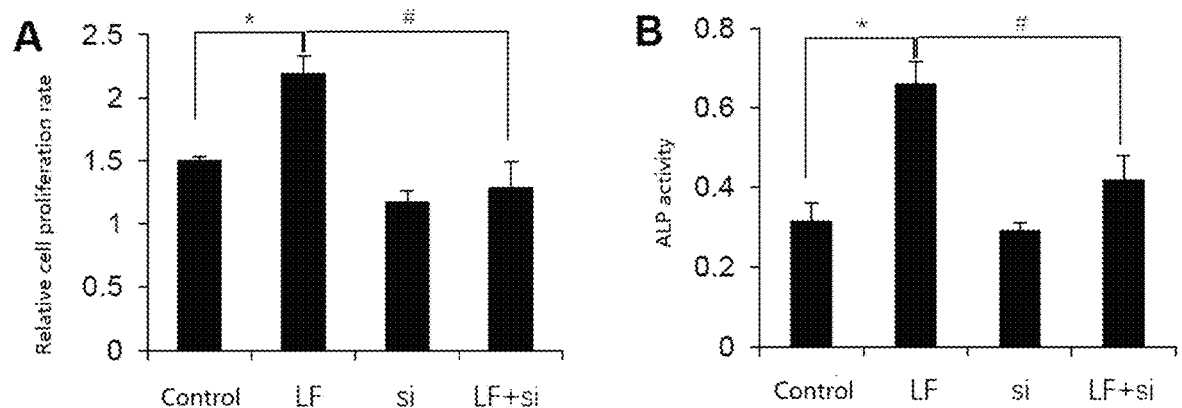
FIGS. 3A and 3B show the effect of adding VDR siRNA on the osteoblast proliferation and differentiation promoted by LF according to an embodiment of the present disclosure.

2. The Role of VDR in the Proliferation and Differentiation of Osteoblasts Promoted by Lactoferrin Based on transcriptome data, the inventors verified that LF can promote the high expression of VDR at both the gene and protein levels. In order to confirm the role of this pathway in the promotion of osteoblast proliferation and differentiation by LF, the inventors first designed a VDR siRNA to achieve the purpose of transiently silencing VDR genes. The principle of siRNA is the post-transcriptional gene silencing mechanism that blocks the expression of corresponding gene. 20 μM VDR siRNA was added to osteoblasts, the proliferation rate of osteoblasts promoted by LF was detected by MTT method, and the ALP activity of osteoblasts promoted by LF was detected by enzyme-linked immunoassay. As shown in FIG. 3, the addition of VDR siRNA can significantly reduce the proliferation and the ALP activity of osteoblasts promoted by LF, indicating that VDR is involved in the bone-forming activity of LF.

Figure 4:
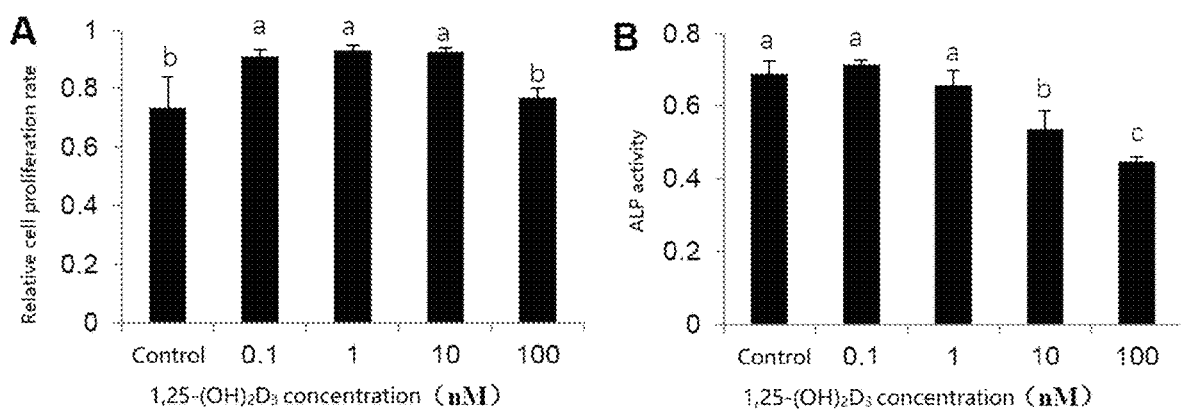
FIGS. 4A and 4B show the effect of lactoferrin together with 1.25(OH)$_2$D$_3$ on the expression of VDR in osteoblasts according to an embodiment of the present disclosure.

3. The Effect of Vitamin D on the Proliferation and Differentiation of Osteoblasts Promoted by Regulating VDR by Lactoferrin The inventors first confirmed that LF promotes the proliferation and differentiation of osteoblasts through the regulation of the VDR pathway using the osteoblast model. Since the osteogenic effect of VDR is mainly achieved by vitamin D, in order to simulate the normal physiological environment, the inventors treated osteoblasts with both 1 nM of 25(OH)$_2$D$_3$ (the active form of vitamin D) and LF, and then studied the proliferation and differentiation of osteoblasts. As shown in FIG. 4, the effect of LF on the proliferation and differentiation of osteoblasts in the presence of vitamin D was explored. As shown in FIG. 4, LF has a stronger effect on promoting the proliferation and differentiation of osteoblasts than 1.25(OH)$_2$D$_3$, and the presence of 1.25(OH)$_2$D$_3$ does not affect the osteogenic activity of LF.

Example 2

1. Effects of Lactoferrin on Blood and Urine Bone Biochemical Markers in Mice

25-OH D$_3$ is an active form of VD in the body, has a longer half-life and is more stable than 1.25(OH)$_2$D$_3$. Generally, the content of VD is reflected by measuring the content of 25-OH D$_3$ in the serum. As shown in Table 1, the 25-OH D$_3$ contents of the respective VD-deficient groups are 50% of that of the corresponding VD-normal groups, but there is no significant difference between the respective oral-administered LF groups and the corresponding control groups, indicating that the addition of VD in feed does cause the increase of 25-OH D$_3$ content in serum, but oral administration of LF has no significant effect on the 25-OH D$_3$ content in serum. As can be seen from the table below, the contents of PTH in the respective VD-deficient groups are significantly higher than that in the corresponding VD-normal groups, and oral administration of 1000 mg/kg BW LF in the VD-deficient group can reduce the PTH content. The contents of calcium and phosphorus in serum reflect the degree of absorption of calcium and phosphorus in the small intestine. The results shows that the calcium and phosphorus contents of the respective VD-normal groups are significantly higher than that of the corresponding VD-deficient groups, indicating that the addition of VD to the feed increases the intake of calcium and phosphorus, which will increase the absorption of calcium and phosphorus in the small intestine, resulting in an increased blood calcium and blood phosphorus content. However, oral administration of LF still has no effect on serum calcium and phosphorus content.

by reducing the excretion of calcium and phosphorus and promoting the reabsorption of calcium and phosphorus by the kidneys.

2. The Effect of Lactoferrin on Bone Mineral Density in Mice

The factors affecting bone mineral density mainly include bone mass factors and bone quality factors. Decreased bone mass is an important factor in the occurrence of common bone diseases, and bone mineral density (BMD) is an important indicator for quantifying bone mass in bone mineral metabolism. The BMD index is of great significance for the prediction of fracture risk, the early diagnosis of osteoporosis and the evaluation of intervention measures. Therefore, in this experiment, bone mineral density values of the femurs (FIG. 6) of the mice in each group were measured 5 months after oral administration of lactoferrin.

Figure 6:
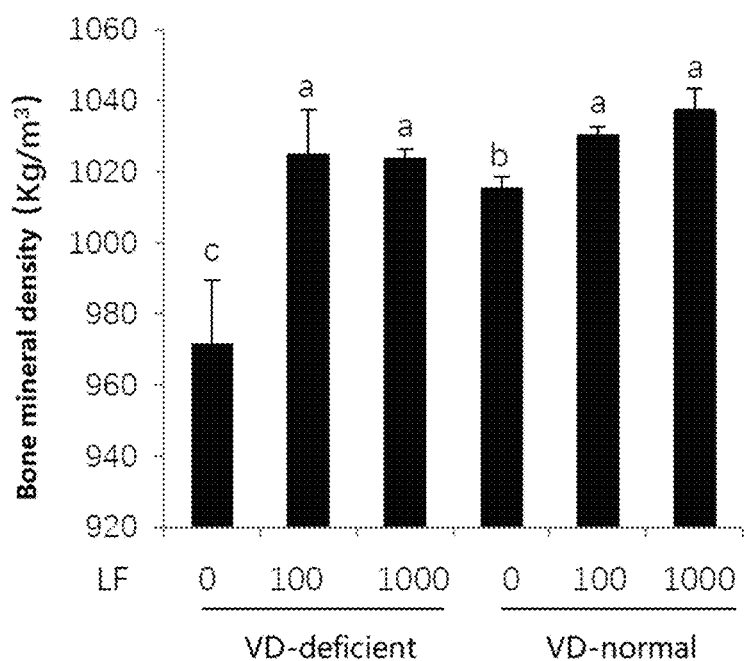
FIG. 6 shows the bone mineral density of the femur of mice in each treatment group according to an embodiment of the present disclosure.

As shown in FIG. 6, the bone mineral density of the femur in the VD-deficient control group is the lowest, while the bone mineral density of the VD-deficient LF100-administered group increases significantly by 5.67% compared with the VD-deficient control group (p<0.05), indicating that in the case of VD deficiency, oral administration of LF can increase bone mineral density in mice. The bone mineral density of the VD-normal control group is significantly higher than that of the VD-deficient control group, but has no significant difference from the VD-deficient LF100-administered group, indicating that oral administration of 100 mg/kg of LF can compensate for the low bone mineral density caused by VD-deficient. When VD is normal, oral administration of lactoferrin can further promote bone mineral density, but the effect is not as significant as when VD is lacking, indicating that LF has the same effect on bone mineral density in mice as VD.

TABLE 1

Contents of blood biochemical markers in mice of each group

| | VD-deficient control group | VD-deficient LF100-administered group | VD-deficient LF100-administered group | VD-normal control group | VD-normal LF100-administered group | VD-normal LF100-administered group |
|---|---|---|---|---|---|---|
| 25-OH VD3 (ng/mL) | 16.70 ± 3.49$^a$ | 15.02 ± 4.2$^a$ | 14.8 ± 2.39$^a$ | 30.14 ± 2.89$^b$ | 29.67 ± 2.45$^b$ | 27.61 ± 2.93$^b$ |
| PTH (pg/mL) | 111.23 ± 15.27$^a$ | 116.09 ± 16.06$^a$ | 93.69 ± 34.61$^b$ | 88.66 ± 22.51$^b$ | 80.87 ± 13.56$^b$ | 91.91 ± 13.10$^b$ |
| Ca (mmol/L) | 1.69 ± 0.19$^a$ | 1.57 ± 0.28$^a$ | 1.6 ± 0.13$^a$ | 2.49 ± 0.35$^b$ | 2.42 ± 0.23$^b$ | 2.25 ± 0.17$^b$ |
| P (mmol/L) | 2.29 ± 0.23$^a$ | 2.06 ± 0.11$^a$ | 2.33 ± 0.42$^a$ | 2.78 ± 1.35$^b$ | 2.85 ± 0.54$^b$ | 2.26 ± 0.33$^a$ |

Mean ± SD, labeling with different letters a, b, and c in the same row means significant difference, n = 8, p < 0.05.

Figure 5:
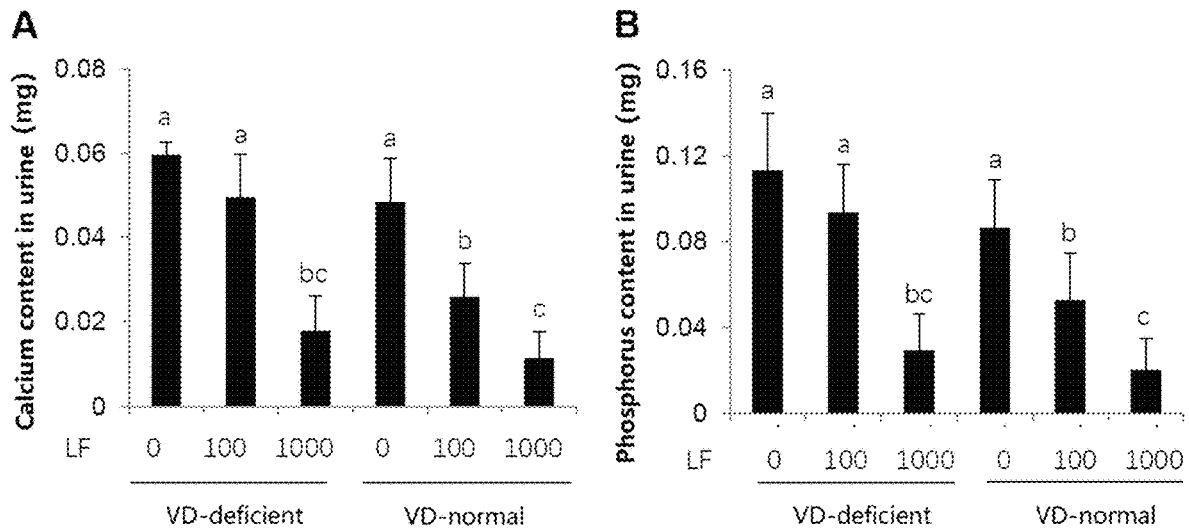
FIGS. 5A and 5B show the contents of calcium and phosphorus in the urine of mice of each group according to an embodiment of the present disclosure.

In order to reflect the reabsorption of calcium and phosphorus by the kidney, the contents of calcium and phosphorus in urine were measured. The results are shown in FIG. 5. In the VD-deficient groups, the calcium content in the LF1000 group is reduced by 67% compared with the control group, and the phosphorus content in the LF1000 group is reduced by 72% compared with the control group; in the VD-normal groups, the calcium content in the LF1000 group is reduced by 80% compared with the control group, and the phosphorus content in the LF1000 group is reduced by 78% compared with the control group. It shows that the addition of 1000 mg lactoferrin/kg BW can significantly reduce the contents of calcium and phosphorus in the urine 3. The Effect of Lactoferrin on the Microstructure of Mouse Femoral Trabecula According to the micro-building theory, the strength of the trabecular bone depends not only on the BMD, but also on its three-dimensional structure. In pathology, bone damage should include both "quantitative" change and "qualitative" changes. Quantitative change is the decline of BMD, while qualitative change is the change of the microstructure of trabecular bone, such as trabecular number and thickness, trabecular connection, and so on. Trabecular bone plays a major role in the microstructure. Increasing the cross structure of each trabecular bone can increase the supporting strength of the bone, but has basically no effect on bone mineral density. Therefore, in order to comprehensively analyze the promoting effect of lactoferrin on bone health, in addition to bone mineral density, the microstructure of trabecular bone must be studied. Therefore, in this experiment, the morphology and structure of trabecular bone were analyzed using micro-CT three-dimensional reconstruction technology to further evaluate the effect of lactoferrin on trabecular bone.

The distal femur is considered a sensitive site for detecting bone health due to high cancellous bone content and rapid bone turnover. Therefore, the inventors analyzed the trabecular pattern factor is used to evaluate the morphology of the trabecular bone. This parameter is determined by the surface area and volume of the trabecular bone, and is a parameter obtained through 3D simulation. The smaller the TPF value, the better the connectivity between trabecular bones. BV/TV, Tb·Th, Tb·N, and Tb·Sp are parameters that can be provided by both micro-CT and bone tissue morphometry. The TPF value is a parameter based on the analysis of the three-dimensional structure of the trabecular bone, can be obtained from micro-CT analysis, but cannot be provided by the traditional two-dimensional method.

TABLE 2 trabecular structure parameters of femoral ROI region of mice in each group

| | VD-deficient control group | VD-deficient LF100-administered group | VD-deficient LF100-administered group | VD-normal control group | VD-normal LF100-administered group | VD-normal LF100-administered group |
|---|---|---|---|---|---|---|
| BV/TV (%) | $0.2 \pm 0.027^c$ | $0.306 \pm 0.028^a$ | $0.252 \pm 0.029^b$ | $0.253 \pm 0.011^b$ | $0.327 \pm 0.053^a$ | $0.28 \pm 0.017^{ab}$ |
| Tb · Th (mm) | $0.043 \pm 0.001^c$ | $0.049 \pm 0.004^b$ | $0.054 \pm 0.005^{ab}$ | $0.043 \pm 0.005^{bc}$ | $0.058 \pm 0.003^a$ | $0.057 \pm 0.004^{ab}$ |
| Tb · N ($mm^{-1}$) | $4.468 \pm 0.528^b$ | $5.411 \pm 0.447^{ab}$ | $5.374 \pm 0.501^{ab}$ | $5.398 \pm 0.749^{ab}$ | $6.022 \pm 0.112^a$ | $6.029 \pm 0.586^a$ |
| Tb · Sp (mm) | $0.183 \pm 0.018^a$ | $0.131 \pm 0.017^b$ | $0.136 \pm 0.017^b$ | $0.169 \pm 0.041^{ab}$ | $0.126 \pm 0.012^b$ | $0.141 \pm 0.020^b$ |
| TPF ($mm^{-1}$) | $10.826 \pm 1.779^a$ | $4.484 \pm 0.845^b$ | $7.290 \pm 2.128^{ab}$ | $7.557 \pm 1.870^{ab}$ | $5.025 \pm 0.738^b$ | $5.599 \pm 0.397^b$ |

Mean ± SD, labeling with different letters a, b, and c in the same row means significant difference, n = 8, p < 0.05.

microstructure of trabecular bone of the distal femur using micro-CT. Preliminary analysis showed that there was no difference in the cortical bones of the mice in each group, but the difference in the cancellous bone was obvious. Therefore, this study mainly analyzed the microstructure of the cancellous trabecular bone of the femur in each group. The three-dimensional structure image of the trabecular bone of the ROI region of the mouse femur obtained by micro-CT reconstruction is shown in FIG. 7A and the longitudinal section is shown in FIG. 7B.

Figure 7:
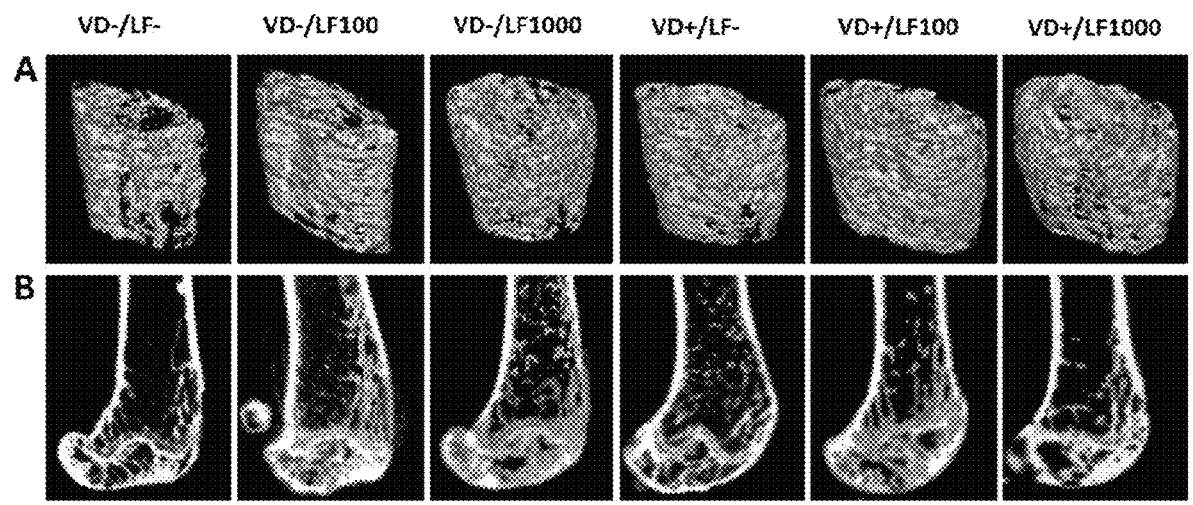
FIGS. 7A and 7B show the three-dimensional microstructure of the femur of mice in each treatment group (n=8) according to an embodiment of the present disclosure, where 7A shows the microstructure of the trabecular bone in the ROI region and 7B shows the longitudinal section of the distal femur.
Figure 8:
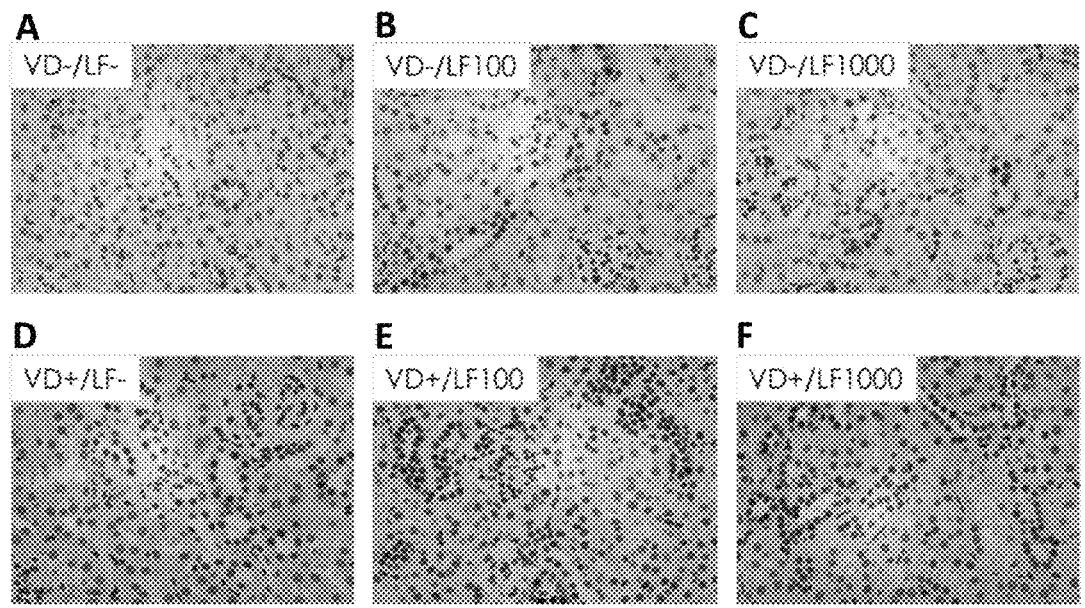
FIGS. 8A-8F show the expression of VDR in the kidneys of mice in each group of oral-administered lactoferrin by immunohistochemistry according to an embodiment of the present disclosure.

From the longitudinal section image of the tibia in FIG. 7, we can see that the trabecular bones of the tibia and femur of the mice in VD-deficient control group are severely lost, and a large cavity is formed at the center of the femur; while there is obviously more trabecular bones and smaller cavity formed in the mice in VD-deficient LF-administered group than the control group. The trabecular bones of mice in the LF groups at the high and low doses are significantly more than that of the control group, with local sparsity still existing and cavities formed. In order to quantitatively analyze the structure of the trabecular bone, the spatial structure parameters of the trabecular bone of the ROI region shown in FIG. 7 were also measured. The results are shown in Table 2. Trabecular bone structure parameters include the followings: Bone Volume Fraction (BV/TV), which is the ratio of the total volume of voxels representing the bone structure in the ROI to the total volume of all voxels in the region, and when the bone is unhealthy, the trabecular bone is lost and the BV/TV value decreases; trabecular thickness (Tb·Th), which is the average thickness of trabecular bone, and when the bone is unhealthy, the value of Tb·Th decreases, and in porous materials, Tb·Th can be understood as thickness of the pore wall; trabecular number (Tb·N), which is the number of intersections of bone tissue and non-bone tissue within a given length, and when the bone is unhealthy, the value of Tb·N decreases; trabecular separation (Tb·Sp), which is the average width of the medullary cavity between the trabecular bones. An increase in Tb·Sp indicates an increased bone resorption and possible bone loss. Tb. Sp can be understood as porosity. The Based on the reconstructed image of the trabecular ROI region of femur in FIG. 7A and the results of the trabecular spatial structural parameters in the ROI region determined in Table 2, it can be seen that the BV/TV and Tb·Th of the VD-deficient control group are significantly lower than those of the oral-administered LF groups (p<0.05), while Tb·Sp and TPF are significantly higher than those of the oral-administered LF groups (p<0.05). It shows that after undergoing a VD-deficient diet, mouse femurs shows significant trabecular bone incompleteness, decreased trabecular thickness and connection density, widened trabecular gap and other structural changes, indicating that the lack of VD will indeed cause the loss of trabecular bone and cause unhealthy bones. In the VD-normal oral-administered LF group, all parameters are comparable to the control group, except for Tb·Th value, which is significantly different from the control group, indicating that the enhancement effect of oral-administered LF on trabecular bone is not obvious when the VD diet is normal.

In the VD-deficient groups, the BV/TV of the trabecular bone of the low-dose LF group is significantly higher than that of the VD-deficient control group and the VD-normal control group, and has no significant difference from the VD-normal LF-administered group. It shows that LF can not only compensate for the loss of trabecular bone caused by the lack of VD, but also achieve a stronger effect than VD. Combined with FIG. 7 and Table 2, it can be seen that the trabecular bone of mice in the LF group is denser, stronger, and more complete in spatial connection than the VD-deficient control group. It shows that LF significantly improves the three-dimensional structure of the loss of trabecular bone in mice caused by the lack of VD, and has an effect of activating bone rebuilding and promoting bone formation. This effect can effectively replace the effect of VD on bone health and make up for bone damage caused by VD deficiency.

4. The Effect of Lactoferrin on the Expression of VDR in Mouse Kidney, Colon and Bone Tissue The immunohistochemical technique was used to detect the expression of VDR in kidney tissues. As shown in FIG.

8, the cells with nuclei stained brown are positive cells for high expression of VDR. The inventors found that each treatment group had VDR expression, and the number of VDR positive cells in the VD-normal group was significantly more than that in the VD-deficient group, and the number of VDR positive cells in the oral-administrated lactoferrin group was more than that in the control group. The results show that under normal VD conditions, LF can significantly increase the expression of VDR, and in the case of VD deficiency, LF can make up for the lack of VDR expression.

Figure 9:
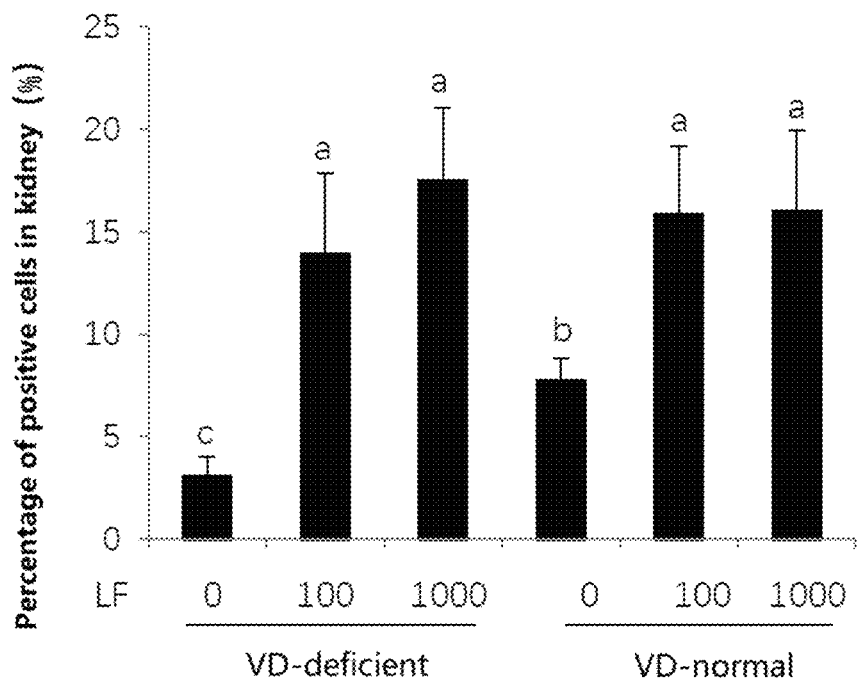
FIG. 9 shows quantitative analysis of VDR in the kidneys of mice in each group of oral-administered lactoferrin by immunohistochemistry according to an embodiment of the present disclosure.

The positive cells for VDR expression in the kidney for each treatment group are shown in FIG. 9, in which the cells with nuclei stained brown are positive cells for VDR expression. It can be seen from the figure that oral administration of lactoferrin can significantly promote the expression of VDR in the kidney cell nucleus. The quantitative analysis is shown in FIG. 9. As shown, the VD-deficient control group has a VDR-positive cell rate of only 3%; the VD-deficient LF100-administered group has a VDR-positive cell rate of 13.8%; the VD-deficient LF1000-administered group has a VDR-positive cell rate of 17%; the VD-normal control group has a VDR-positive cell rate of 7.5%; the VD-normal LF100-administered group has a VDR-positive cell rate of 16.3%; and the VD-normal LF1000-administered group has a VDR-positive cell rate of 16.5%. It follows that, the VDR-positive cell rate in the VD-normal LF1000-administered group is about twice as much as that in the control group, that is, the oral-administered LF normal group significantly promotes VDR expression.

Figure 10:
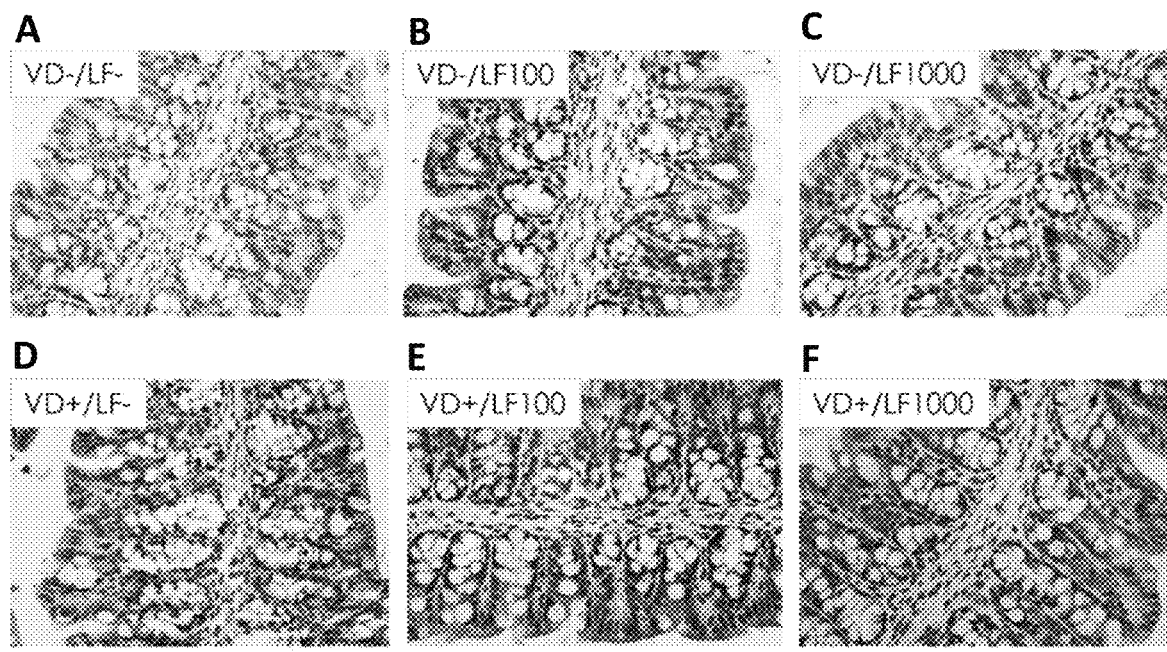
FIGS. 10A-10F show the expression of VDR in the colon of mice in each group of oral-administered lactoferrin by immunohistochemistry according to an embodiment of the present disclosure.
Figure 11:
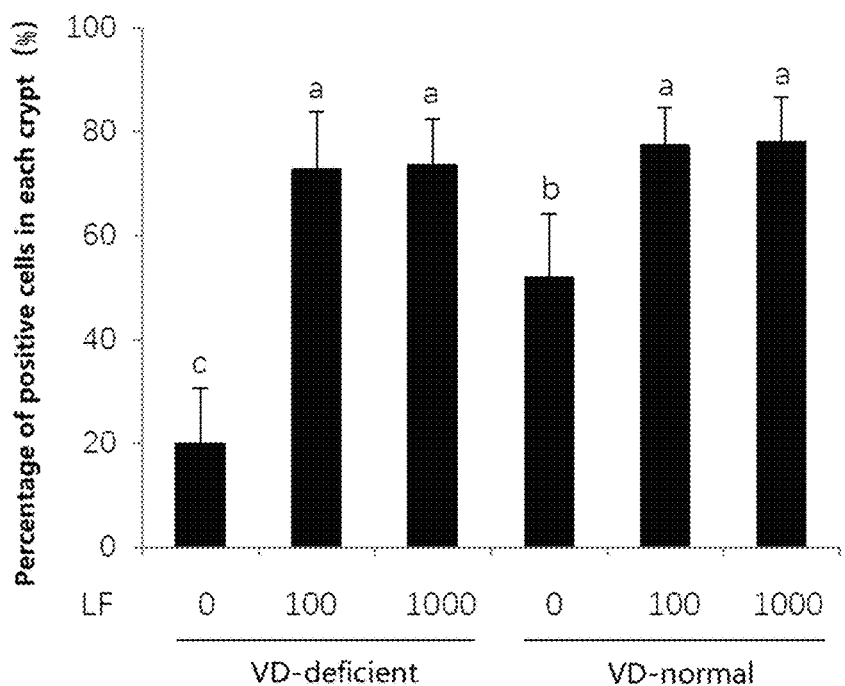
FIG. 11 shows quantitative analysis of VDR in the colon of mice in each group of oral-administered lactoferrin by immunohistochemistry according to an embodiment of the present disclosure.

The positive cells for VDR expression in the colon for each treatment group are shown in FIG. 10, in which the cells stained brown are positive cells for VDR expression. The figure shows that the positive cells are mainly distributed in the crypts. Therefore, the inventors reflect the difference in VDR expression of individual groups by calculating the proportion of positive cells to the total cells in each crypt, and the results are shown in FIG. 11. As shown, the VD-deficient control group has a positive cell rate of 20%, while the VD-deficient LF-administered group has a positive cell rate of more than 70%; the VD-normal control group has a positive cell rate of 50%, and the VD-normal oral-administered LF group has a positive cell rate of nearly 80%. It follows that, LF can significantly promote the high expression of VDR in the colon, and the effect of LF is stronger than that of VD.

Figure 12:
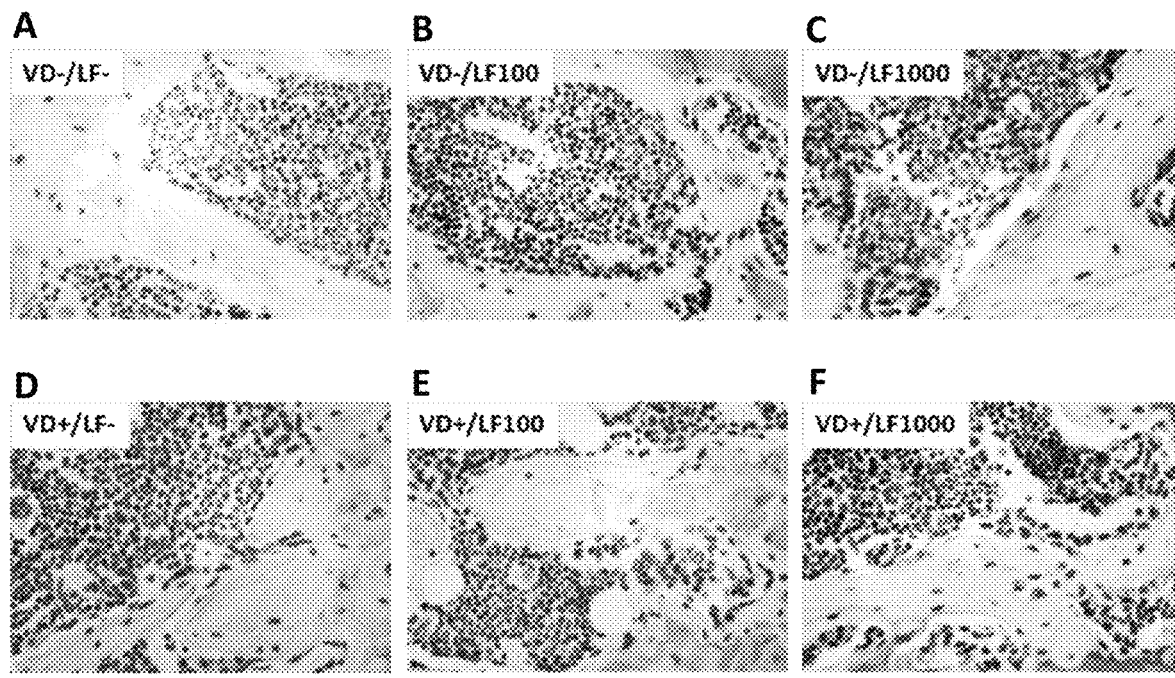
FIGS. 12A-12F show the expression of VDR in the tibia of mice in each group of oral-administered lactoferrin by immunohistochemistry according to an embodiment of the present disclosure.
Figure 13:
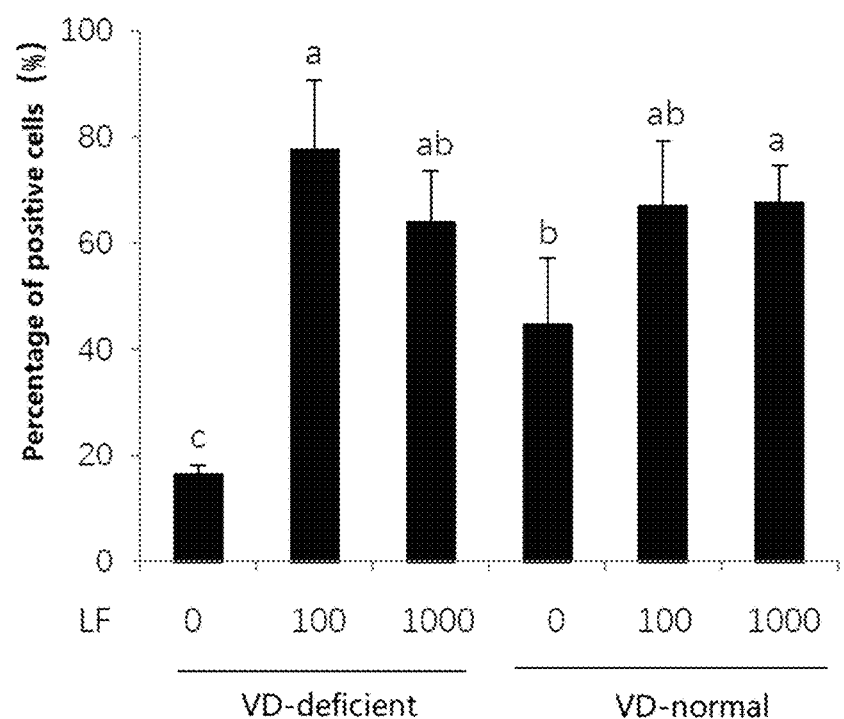
FIG. 13 shows quantitative analysis of VDR in the tibia of mice in each group of oral-administered lactoferrin by immunohistochemistry according to an embodiment of the present disclosure.

The positive cells for VDR expression in the femur for each treatment group are shown in FIG. 12, in which osteoblasts are distributed at the edge of the trabecular bone, and the cells stained brown are positive cells for VDR expression. It can be seen from the figure that the positive cells in the oral-administered LF group are significantly more than those in the control group. The quantitative analysis is shown in FIG. 13. As shown, the VD-deficient control group has the lowest positive cell rate of 15%, the VD-deficient LF100-administered group has the highest positive cell rate of 75%, the positive cell rate of the VD-normal control group is 3 times higher than that of the VD-deficient control group, and the positive cell rate of the VD-normal oral-administered lactoferrin group is higher than that of the control group by 20%. It shows that lactoferrin can significantly promote the expression of VDR in osteoblasts, and the promotion effect of VD on VDR is more significant than that of VD.

5. Western Blot Detection of VDR Expression in Kidney, Colon and Bone Tissue

The inventors further verified the expression of VDR in three major tissues, kidney, colon and bone using the Western blot method by extracting the tissue protein.

Figure 14:
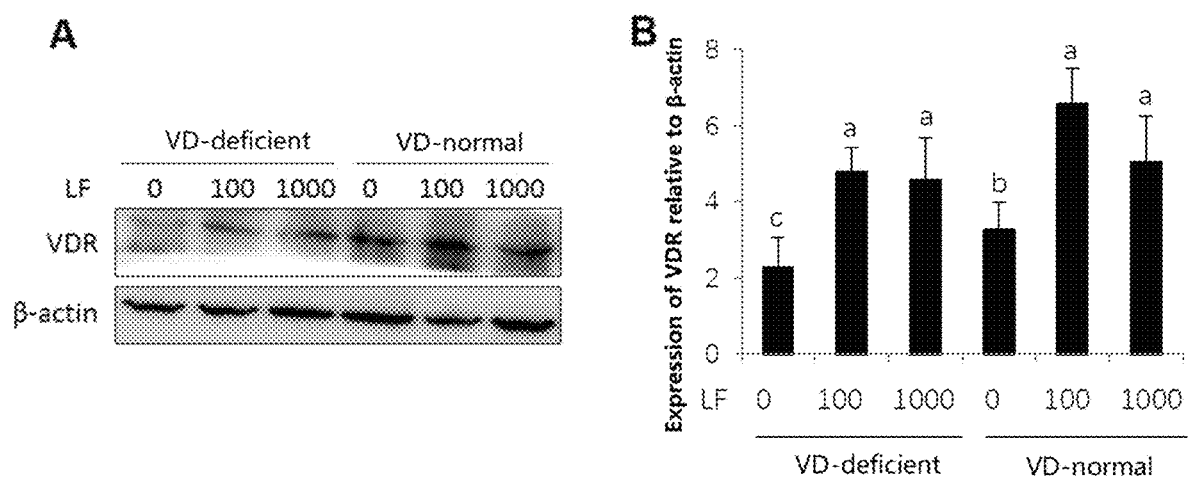
FIGS. 14A-14B show the expression level and quantitative analysis of VDR in the kidney in each treatment group according to an embodiment of the present disclosure.

The results of VDR expression in the kidney are shown in FIG. 14. As shown, oral administration of lactoferrin at different doses can promote VDR expression. In the case of VD deficiency, lactoferrin can still effectively promote the expression of VDR, and the promotion effect is stronger than that of VD per se, indicating that lactoferrin is a more effective VDR agonist than vitamin D. In addition, in the case of a normal VD diet, oral administration of lactoferrin can also effectively promote VDR expression. The VD-normal LF100 group has the strongest promotion effect on VDR expression, almost twice as higher as that of the VD normal control group, indicating that no matter whether VD exists or not, lactoferrin can promote the high expression of VDR.

Figure 15:
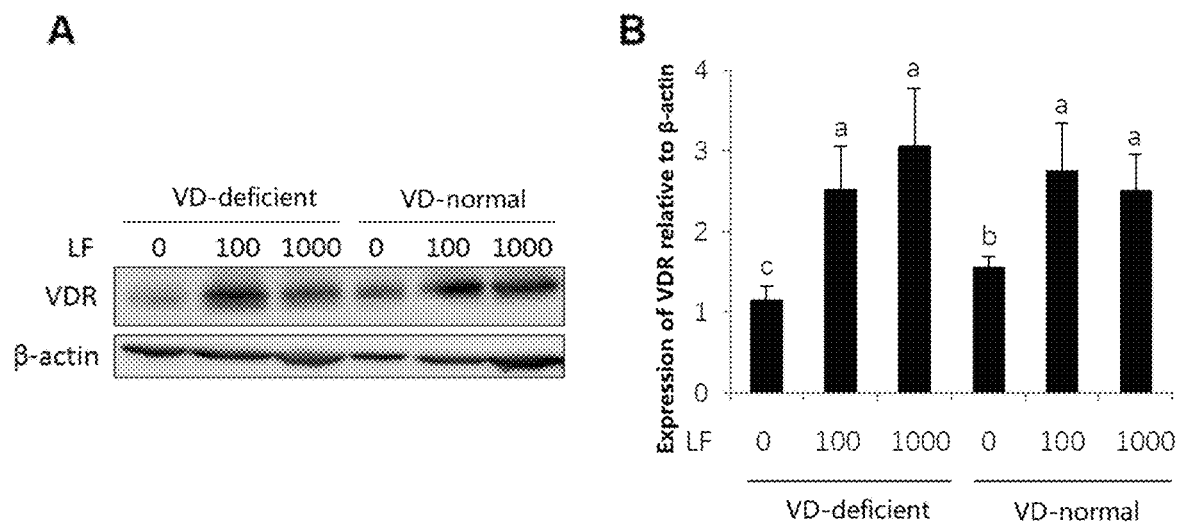
FIGS. 15A-15B show the expression level and quantitative analysis of VDR in the colon in each treatment group according to an embodiment of the present disclosure.

The expression of VDR in the colon is shown in FIG. 15. Similar to the result in the kidney, the addition of lactoferrin can effectively promote the expression of VDR in the colon, and the effect of lactoferrin is stronger than that of vitamin D.

Figure 16:
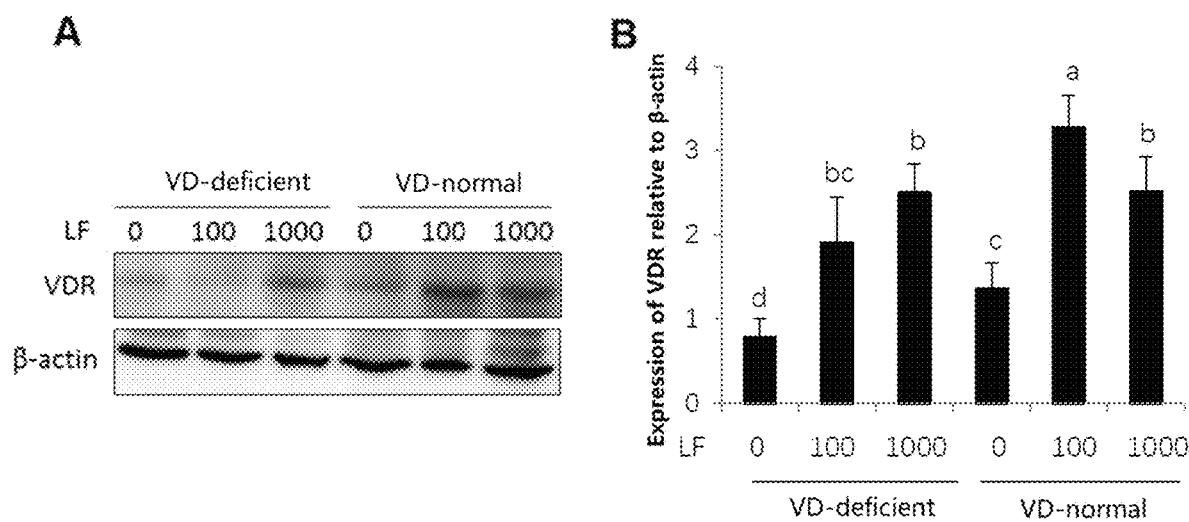
FIGS. 16A-16B show the expression level and quantitative analysis of VDR in the femur in each treatment group according to an embodiment of the present disclosure.

The expression of VDR in the femur is shown in FIG. 16. As shown, the expression of VDR in the VD-normal diet group is higher than that in the VD-deficient diet group, indicating that LF significantly promotes the expression of VDR in the femur. The VD-normal oral-administered 100 mg LF/kg BW group has the highest expression of VDR, 2.35 times higher than that of the VD normal control group, indicating that LF can significantly promote the expression of VDR when VD is normal. In the case of VD deficiency, the LF1000-administered group has the strongest effect on VDR expression, 3 times higher than that of the control group, and significantly different from that of the VD normal control group, indicating that LF can alleviate insufficient VDR synthesis caused by VD deficiency, and this effect is stronger than that of VD.

Example 3

Figure 17:
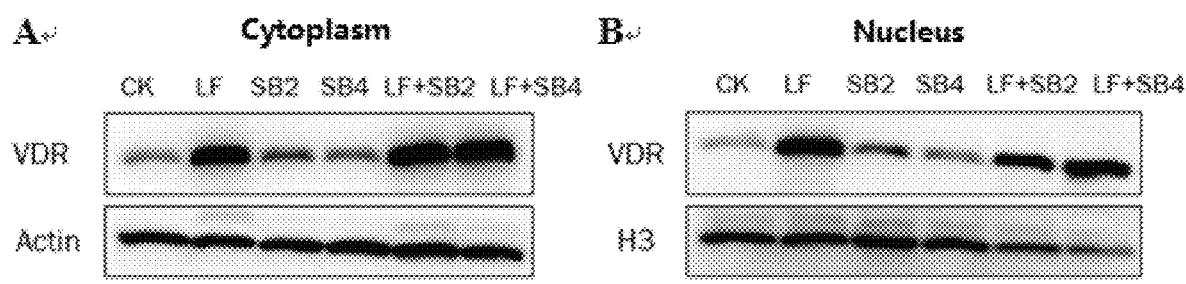
FIGS. 17A-17B show the effect of inhibitors SB203580 and SB431542 on the LF-promoted VDR expression according to one embodiment of the present disclosure.

1. The Effect of Inhibiting p38 and TGF-β/Smads Signaling Pathway on the Expression of VDR Promoted by Lactoferrin In order to verify the mechanism of LF for promoting the high expression of VDR, firstly, inhibitors were used in the cytoplasm to inhibit the extracellular signaling pathway to detect the promotion effect of LF on VDR. The results are shown in FIG. 17A. The p38 inhibitor SB203580 and the TGF-β/smads pathway inhibitor SB431542 were added to detect the expression of VDR promoted by LF. As shown, the addition of respective inhibitors has no significant effect on the expression of VDR promoted by LF, indicating that the promotion of LF on intracytoplasmic VDR is not regulated by p38 pathway or TGF-β/smads pathway.

Since VDR mainly functions in the nucleus, after inhibiting the pathway using SB203580 and SB431542 inhibitors, the expression of VDR promoted by LF in nucleus was detected. The results are shown in FIG. 17B. As shown, the addition of respective inhibitors has no significant effect on the expression of VDR promoted by LF, indicating that the promotion effect of LF on nuclear VDR is not regulated by the p38 pathway or the TGF-β/smads pathway.

Figure 18:
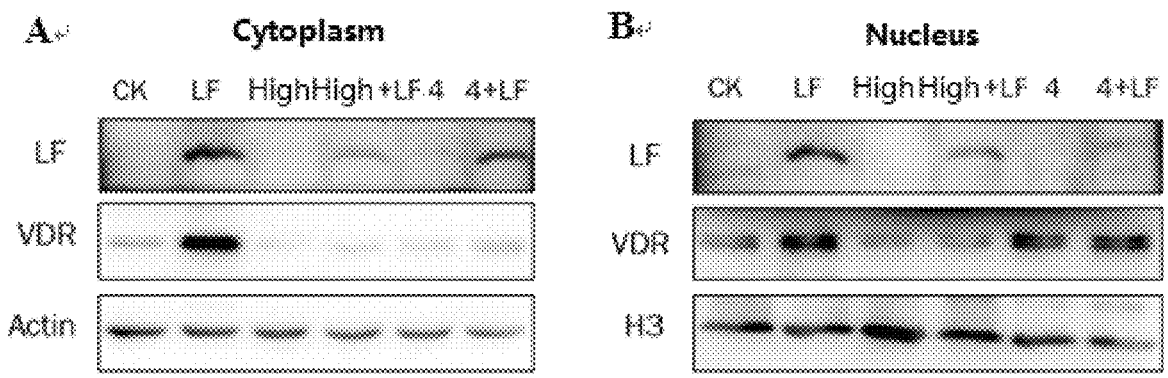
FIGS. 18A-18B show the effect of hypertonicity and 4° C. culture on the LF-promoted VDR expression in MC3T3-E1 cells according to one embodiment of the present disclosure.

2. The Effect of Inhibition of Endocytosis on the Expression of VDR Promoted by Lactoferrin Studies have shown that LF can directly enter the cell and bind with DNA to regulate cell gene expression. Therefore, in order to study the effect of endocytosis, cells were stimulated with LF under culture conditions that inhibit endocytosis, and the inhibitory effect on the endocytosis of LF were detected firstly. As shown in FIG. 18, both hypertonic and 4° C. environments can better inhibit the endocytosis of LF. Then, the promotion effect of LF on VDR was measured to analyze whether the inhibition of endocytosis affected the expression of VDR promoted by LF to determine the site of action of LF. The results are shown in FIG. 18. Under the condition of inhibiting endocytosis, the promotion effect of LF on the expression of VDR in the cytoplasm and nucleus can be significantly inhibited, indicating that LF promotes the expression of VDR by entering the cell, not by stimulating the extracellular signal pathway.

In the description of this specification, the description with reference to the terms "one embodiment", "some embodiments", "an example", "specific examples", or "some examples" and the like means that the specific feature, structure, material, or characteristic described in combination with the embodiment or example is included in at least one embodiment or example of the present invention. In this specification, the schematic expressions of the above terms are not necessarily directed to the same embodiment or example. Furthermore, the particular features, structures, materials, or characteristics described may be combined in any suitable manner in any one or more embodiments or examples. In addition, if not contradictory, different embodiments or examples and features of the different embodiments or examples described in this specification may be combined by those skilled in the art.

Although the embodiments of the present disclosure have been shown and described above, it can be understood that the above embodiments are exemplary and should not be construed as limitations on the present disclosure. Those of ordinary skill in the art can make changes, modifications, and substitutions to the above-mentioned embodiments within the scope of the present invention.

What is claimed is:

1. A method of treating Vitamin D (VD)-deficient osteoporosis, comprising administering to a patient in need thereof lactoferrin at a dose of 100 mg/kg Body Weight (BW),
wherein Vitamin D Receptor (VDR) gene and protein levels increase in the patient.

2. The method according to claim 1, wherein administration of the lactoferrin increases expression of the VDR gene by 25 to 35 times.

3. The method according to claim 1, wherein administration of the lactoferrin promotes proliferation and differentiation of osteoblasts via increase in the VDR gene and the protein levels.

4. The method according to claim 1, further administering vitamin D.

5. The method according to claim 4, wherein the vitamin D is in a form of 25-OH $D_3$ or $1.25(OH)_2D_3$.

6. The method according to claim 1, wherein the method maintains blood calcium balance by increasing reabsorption of calcium and phosphorus by the kidney, decreases calcium in urine, and promotes bone calcium deposition.

7. The method according to claim 1, wherein administration of the lactoferrin increases bone mineral density of the VD-deficient bone osteoporosis.

8. The method according to claim 1, wherein administration of the lactoferrin improves microstructure of trabecular bone of the VD-deficient bone osteoporosis.

9. The method according to claim 1, wherein administration of the lactoferrin promotes expression of the VDR gene in the kidney, bone or colon.

10. The method according to claim 1, wherein administration of the lactoferrin activates a VDR signaling pathway via endocytosis.

11. The method of claim 5, wherein the concentration of $1.25(OH)_2D_3$ is 0.1 to 10 nM.

12. A method of treating Vitamin D (VD)-deficient osteoporosis, comprising administering to a patient in need thereof lactoferrin at a dose of 100 mg/kg Body Weight (BW) and $1.25(OH)_2D_3$,
wherein the concentration of $1.25(OH)_2D_3$ is 1 or 10 nM, and
wherein Vitamin D Receptor (VDR) gene and protein levels increase in the patient.

* * * * *